(12) United States Patent
Tsukui

(10) Patent No.: US 8,367,391 B2
(45) Date of Patent: Feb. 5, 2013

(54) METHOD FOR DETECTING OR DETERMINING ABNORMAL PRION PROTEIN ASSOCIATED WITH TRANSMISSIBLE SPONGIFORM ENCEPHALOPATHY IN BLOOD-DERIVED SPECIMEN OR BODY FLUID-DERIVED SPECIMEN

(75) Inventor: Kazuo Tsukui, Minato-ku (JP)

(73) Assignee: Japanese Red Cross Society, Minato-ku, Tokyo (JP)

( * ) Notice: Subject to any disclaimer, the term of this patent is extended or adjusted under 35 U.S.C. 154(b) by 425 days.

(21) Appl. No.: 12/674,857

(22) PCT Filed: Aug. 22, 2008

(86) PCT No.: PCT/JP2008/065470
§ 371 (c)(1),
(2), (4) Date: Feb. 23, 2010

(87) PCT Pub. No.: WO2009/025396
PCT Pub. Date: Feb. 26, 2009

(65) Prior Publication Data
US 2011/0053791 A1    Mar. 3, 2011

(30) Foreign Application Priority Data

Aug. 23, 2007  (JP) .................................. 2007-217203

(51) Int. Cl.
*C12N 7/02*     (2006.01)
*C12P 21/06*   (2006.01)
*C07K 1/30*    (2006.01)
*C12Q 1/70*    (2006.01)
(52) U.S. Cl. ............ 435/239; 435/68.1; 435/5; 530/427
(58) Field of Classification Search .................. 435/239, 435/68.1, 5; 530/427
See application file for complete search history.

(56) References Cited

U.S. PATENT DOCUMENTS 6,780,979 B1 * 8/2004 Deslys ........................ 530/412
2005/0170519 A1   8/2005 Alam

FOREIGN PATENT DOCUMENTS

| JP | 10-267928 | 10/1998 |
|---|---|---|
| JP | 11-32795 | 2/1999 |
| WO | WO 01/38354 | 5/2001 |
| WO | WO 2005/001481 | 1/2005 |

OTHER PUBLICATIONS

European Search Report from EP Application No. 08792796.8 dated Nov. 25, 2010.
European Search Report from EP Application No. 08792796.8 dated Dec. 22, 2010.
Polson et al. "Optimization of protein precipitation based upon effectiveness of protein removal and ionization effect in liquid chromatography—tandem mass spectrometry." *J. of Chroma.* vol. 785. 2003.. pp. 263-275.

(Continued)

*Primary Examiner* — Rosanne Kosson
(74) *Attorney, Agent, or Firm* — Merchant & Gould P.C.

(57) ABSTRACT

A pretreatment method of a specimen used for detecting or determining abnormal prion protein (PrPres) associated with transmissible spongiform encephalopathy (TSE), wherein (1) a specimen which had been treated with proteinase K is heated in the presence of sodium dodecyl sulfate (SDS) to dissolve proteins and inactivate infectious activity in the specimen at the same time; (2) the specimen processed in the above (1) is cooled under a neutral condition to make abnormal prion protein (PrPres) associated with transmissible spongiform encephalopathy (TSE) aggregated; (3) the aggregate formed in the above (2) is separated from a solution; and (4) the separated PrPres aggregate is detected by the ultrasensitive chemiluminescence method.

9 Claims, 5 Drawing Sheets

OTHER PUBLICATIONS

Figure 1:
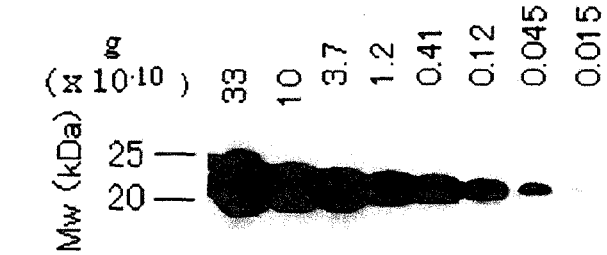
Figure 1:
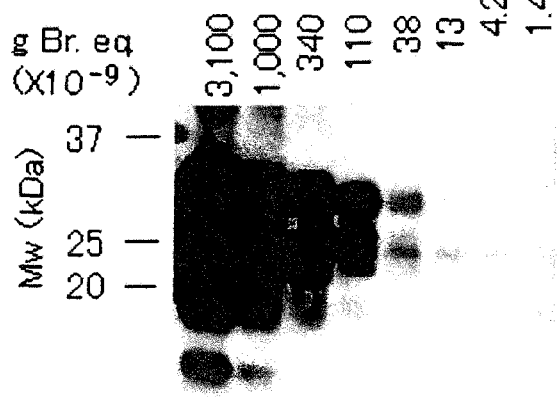

Hill et al. "Investigation of variant Creutzfeldt-Jakob disease and other human prior diseases with tonsil biopsy samples." *The Lancet*. vol. 353. 1999. pp. 183-189.

Frosh et al. "Analysis of 2000 consecutive UK tonsillectomy specimens for disease-related prion protein." *The Lancet*. vol. 364. 2004. pp. 1260-1262.

Castilla et al. "Detection of prions in blood." *Nature Medicine*. vol. 11. 2005. pp. 982-985.

Pan et al. "Detection of misfolded prion protein in blood with conformationally sensitive peptides." *Transfusion*. vol. 47. 2007. pp. 1418-1425.

Chang et al. "Test of Detection of Disease-Associated Prion Aggregate in the Blood of Infected but Asymptomatic Animals." *Clin. and Vaccine Immun*. vol. 14. No. 1. 2007. pp. 36-43.

Deleault et al. "Formation of native prions from minimal components in vitro." *PNAS*. vol. 104. No. 23. 2007. pp. 9741-9746.

Saa et al. "Presymptomatic Dection of Prions in Blood." *Science*. vol. 313. 2006. pp. 92-94.

Haraguchi "Prion Atarashii Seimeitai eno Chosen Kansenryoku o Yoshi Zoshoku suru "Tanpakushitsu" no Shotai wa?"*Kagaku to Seibutsu*. vol. 24. No. 3. 1986. pp. 142-143.—No Translation.

Tsukui et al. "A potential blood test for transmissioble spongiform encephalopathies by detecting carbohydrate-dependent aggretgates of PrPres-like proteins in scrapie-infected hamster plasma." *Microbiol. Immunol*. vol. 51. No. 12. 2007. pp. 1221-1231.

Gakumazawa et al. "BSE Screening Kensa ni Ikeru Shori Hoho no Kento."*Dai 53 Kai Hokkaido Veterinary Medical Association Taikai Yokoshu*. vol. 46. No. 8. 2002. pp. 304.—No Translation.

\* cited by examiner

METHOD FOR DETECTING OR DETERMINING ABNORMAL PRION PROTEIN ASSOCIATED WITH TRANSMISSIBLE SPONGIFORM ENCEPHALOPATHY IN BLOOD-DERIVED SPECIMEN OR BODY FLUID-DERIVED SPECIMEN

This application is a National Stage Application of PCT/JP2008/065470, filed 22 Aug. 2008, which claims benefit of Serial No. 2007-217203, filed 23 Aug. 2007 in Japan and which applications are incorporated herein by reference. To the extent appropriate, a claim of priority is made to each of the above disclosed applications.

TECHNICAL FIELD

The present invention relates to a method for detecting or determining abnormal prion protein (PrPre) associated with transmissible spongiform encephalopathy (TSE) in a blood-derived specimen or body fluid-derived specimen, especially a pretreatment method of a specimen used for detecting or determining the same.

BACKGROUND ART

Transmissible spongiform encephalopathy (TSE) is generally called prion disease, includes human Creutzfeldt-Jakob disease, BSE in cattle, scrapie in sheep and goat and the like, and is a disease diagnosed in a wide range of mammals. The common features of these diseases are that mortality after symptom onset is 100%, that antemortem diagnoses of these diseases are extremely difficult, and that these diseases are generally confirmed by pathological diagnosis at necropsy. However, it became clear that variant CJD (vCJD) is infected by transfusion, and a plurality of infection cases have been reported recently. Therefore, life-prolonging procedure and treatment for patients with TSE by antemortem diagnosis, and development of diagnosis of a specimen before symptom onset and antemortem diagnosis of TSE so as to prevent infection spread by horizontal disease transmission via blood and the like have been urgently-required.

The biggest reason that the development of this blood test is difficult is that the most appropriate marker cannot be detected in blood. In general, diagnosis of TSE is performed by detecting prion protein having an abnormal structure ($PrP^{sc}$ or PrPres) as a surrogate marker. This PrPres is a protein molecule distinctively detected after symptom onset. The normal PrP (PrPc) has three $\alpha$-helix regions in a molecule, while PrPres is a conformational isotype having a $\beta$-sheet structure in place of the $\alpha$-helix structure in this PrP molecule. For the reason, PrPres is characterized by having a resistance to digestion action by proteases as well as a remarkable stability of the molecular structure thereof.

The resistance of this protein to proteases is distinctive because this protein is resistant to proteinase K (PK) which is a strong protease and can digest almost all proteins. Only a small portion of the molecule of the abnormal PrP is digested, while almost all other proteins are digested by PK. Therefore, abnormal PrP is represented by "PrPres". The name was made by adding "res" to the end of "PrP".

However, this PrPres is generally confirmed only in the infected sites of animals after symptom onset (the central nerve system, or may be confirmed in the reticuloendothelial system tissue in the case of vCJD). The level of PrPres in blood is extremely small, and thus PrPres cannot be detected by conventional methods. For the above reasons, a detection method by which several to several tens of ng/mL PrPres that had not been able to be detected by conventional methods can be detected, and a method by which PrPres of an individual with the disease can be clearly discriminated from PrPres of a healthy individual, and can be detected using blood. Development of a novel substance specifically binding to PrPres or a novel method for amplifying PrPres has been studied in the world so as to satisfy the requirement.

Conventional methods which had been developed to satisfy the requirement are not sufficient in terms of detection sensitivity or specificity to constitute the blood test, and thus are not practically used. Only a method for amplifying PrPres in vitro to a detectable amount so as to detect PrPres (Peptide Misfolding Cyclic Amplification; PMCA) has been introduced as a method which may be effective to constitute the blood test (Saa, P., Castilla, J., Soto, C. 2006, Science 313: 92-94). However, this PMCA method has two distinctive features that (1) it takes considerable time to amplify PrPres (the detection rate of a detection case using infected hamster blood in which PrePres had been amplified for 21 days was 60%); and that (2) the brain homogenate of a healthy animal must be optionally added as a precursor of PrPres that is necessary in amplification. Regarding the feature (2), there is a possibility that neuroblast homogenate or platelet homogenate may be used in place of the brain homogenate. However, a large amount of the neuroblast homogenate or the platelet homogenate must be cultured, or the platelet of a healthy individual must be always prepared, and thus it appears to be extremely difficult for the neuroblast or platelet homogenate to be practically used. In addition, it was reported that reaction does not occur if a plasma protein is present in a reaction mixture solution in this method (Prion 2008 symposium; Madrid). Therefore, it cannot be said that there is a possibility that the blood test can be practically carried out by this method.

SUMMARY OF THE INVENTION

Consequently, the object of the present invention is to provide a method by which abnormal prion protein (PrPres) associated with transmissible spongiform encephalopathy in a blood specimen can be detected at a high sensitivity in a short period of time by simple procedure steps, and a large number of specimens can be processed at the same time.

Inventors of the present application had studied various matters so as to achieve the above object, and as a result, found that it is the best to utilize the original property of abnormal prion protein (PrPres) associated with transmissible spongiform encephalopathy that abnormal prion protein is only partially degraded when a specimen is treated with a strong protease such as proteinase K, while other proteins are degraded by the enzyme for a blood-derived specimen of an individual infected with an infectious factor of transmissible spongiform encephalopathy.

Accordingly, the present invention provides a pretreatment method of a specimen used for detecting or determining abnormal prion protein (PrPres) associated with transmissible spongiform encephalopathy (TSE) in a blood-derived specimen of an individual infected with an infectious agent of transmissible spongiform encephalopathy, wherein the specimen is treated with a protease.

As a result of the study by the inventors of the present application on various matters so as to achieve the above object, they found that all the proteins present in a specimen can be dissolved, and infectious activity in the specimen can be inactivated at the same time by subjecting the specimen to a heat treatment in the presence of sodium dodecyl sulfate (SDS), and that abnormal prion protein (PrPres) associated with transmissible spongiform encephalopathy can be concentrated and separated by cooling the specimen which had been subjected to the heat treatment under a neutral condition to selectively make PrPres aggregated, and separating this aggregate from a solution under an acidic condition, and completed the present invention.

Accordingly, the present invention further provides a pretreatment method of a specimen used for detecting or determining abnormal prion protein (PrPres) associated with transmissible spongiform encephalopathy (TSE) in a blood-derived specimen of an individual infected with an infectious agent of transmissible spongiform encephalopathy, wherein
(1) the specimen is heated in the presence of sodium dodecyl sulfate (SDS) to dissolve proteins and inactivate infectious activity in the specimen at the same time;
(2) the specimen processed in the above (1) is cooled under a neutral condition to make abnormal prion protein (PrPres) associated with transmissible spongiform encephalopathy (TSE) aggregated; and
(3) the aggregate formed in the above (2) is separated from a solution under an acidic condition.

It is preferable that the specimen should be treated with a protease before the above step (1). This protease is preferably proteinase K.

The sodium dodecyl sulfate concentration at the above step (1) is preferably 3% by weight.

Heating at the above step (1) is performed preferably at 100° C. for 10 minutes.

Cooling under a neutral condition at the above step (2) is performed by cooling preferably to a temperature of −80° C. to 0° C. at a pH of 7.2 to 7.3.

Separation of the aggregate at the above step (3) is performed under an acidic condition, preferably at a pH of 4.5 to 4.6, by centrifugation, for example. The centrifugation process is performed by high-speed centrifugation at a centrifugal acceleration rate of 10,000 to 20,000×g.

The treatment with the protease is preferably performed with 2 units/mL (specific activity of 40 mAnson u/mg protein; 50 μg/ml) proteinase K at a pH of 7.2 to 7.3 at 37° C. for 60 minutes.

The aggregate obtained at the above step (3) is dissolved in a buffer before determination.

For example, the specimen is a blood-derived specimen, or body fluid. For example, the blood-derived specimen is blood, plasma, serum or a hemocyte rinse solution.

The present invention also provides a method for detecting or determining abnormal prion protein (PrPres) associated with transmissible spongiform encephalopathy (TSE), wherein the abnormal prion protein (PrPres) in the processed specimen obtained by the above method is determined by immunoassay.

When a hamster recombinant PrP molecule is determined by the ultrasensitive chemiluminescence method in the above method, detection sensitivity at which the molecule in an amount of $4.4\times10^{-18}$ moles or less can be detected can be obtained. In addition, detection sensitivity at which PrP in an amount of $10^{-9}$ g brain equivalent or less in a 10% uninfected animal brain homogenate can be detected, and sensitivity at which PrPres in an amount of $10^{-7}$ g brain equivalent or less in a 10% scrapie infected hamster brain homogenate can be detected are obtained, and an infectious factor of 1 $ID_{50}$ or less can be detected by the ultrasensitive chemiluminescence method.

The used amount of the blood-derived specimen is several μL, for example. A large number of specimens can be detected or determined at the same time, and the presence or absence of PrPres in the specimen can be determined within three days.

The above immunoassay is a test by ELISPOT assay or a precise assay by western blotting.

According to the method of the present invention, quantitative analysis of abnormal prion protein (PrPres) associated with transmissible spongiform encephalopathy (TSE) in a blood-derived specimen can be carried out.

BRIEF DESCRIPTION OF DRAWINGS

FIG. 1 is an electropherogram showing experimental results on the detection limit (upper portion) of rHaPrP by the ultrasensitive chemiluminescence method, and the detection limit (lower portion) of PrPres in scrapie infected hamster brain homogenate in Example 1.

FIG. 2 is an electropherogram showing experimental results on discrimination of infection from uninfection by the pretreatment with proteinase K in hamster brain homogenates in Example 2.

FIG. 3 is an electropherogram showing experimental results on discrimination of scrapie infection from uninfection by the acidic SDS precipitation method in hamster plasma specimens in Example 3.

FIG. 4 is an electropherogram showing experimental results on discrimination of scrapie infection from uninfection by the acidic SDS precipitation method in a plurality of the hamster plasma specimens in Example 4.

FIG. 5 is an electropherogram showing experimental results on the appearance of a similar pattern of infected hamster plasma by mixing an infected hamster brain homogenate with uninfected hamster plasma in Example 5.

FIG. 6 is a graph showing experimental results on the detection limit of PrP (rHaPrP was used) by the ultrasensitive chemiluminescence method in Example 6.

FIG. 7 is a graph showing experimental results on the detection limit of PrP (a hamster brain homogenate was used) by the ultrasensitive chemiluminescence method in Example 6.

DETAILED DESCRIPTION OF THE INVENTION

Embodiments to Carry Out the Invention

Specimen

The specimen used in the method of the present invention is, for example, a blood-derived specimen or body fluid infected with an infectious agent of transmissible spongiform encephalopathy. For example, the blood-derived specimen is blood, plasma, serum or a hemocyte rinse solution. The method of the present invention is a method by which a large number of specimens can be examined for a relatively short period of time, and thus it is especially useful for the tests of blood specimens obtained from blood donors. Blood is advantageously used as a clinical specimen for a patient.

Pretreatment of Specimens (1) Use of a Protease

Blood contains various proteins. In order to detect a specific protein present in a specimen containing the various proteins, it is preferable to use a means to strictly separate the specific protein from other proteins. Proteinase K (PK) which exhibits a proteolytic action on almost all proteins is preferable as the protease used for strict separation. PrPres has a distinct feature that it is only partially sensitive to PK which is a strong protease. Therefore, it is preferable to make the most of this feature as an effective means. On the other hand, PrPres is not completely unreactive to PK.

For the reason, it is necessary to set conditions for a treatment with PK such that the degradation degree of PrPres is small, and other proteins are degraded. Conditions using 2 units/mL (in the case of using an enzyme having specific activity of 40 mAnson u/mg protein, 50 µg/mL) proteinase K at a pH of 7.2 to 7.3 at 37° C. for 60 minutes are preferable. A small portion of PrPres is digested under the conditions, while other proteins are sufficiently degraded, whereby remaining PrPres can be efficiently detected and identified.

(2) Use of SDS

SDS is generally used to disrupt the conformations of protein molecules in the biochemical field. The conformations of almost all protein molecules are disrupted by addition of SDS, and as a result, the proteins become soluble. Therefore, the molecular weights of protein molecules can be determined, irrespective of the specific conformation of each protein molecule. However, it is presumed that the PrPres molecules are formed into strong aggregates, due to its β-sheet structure. Formation of aggregates occurs in the presence of SDS. PrPres is remarkably different from other proteins in this feature. Other proteins are made soluble in the presence of SDS, and PrPres formed into aggregates is made precipitated, using the feature of PrPres in the method of the present invention.

The transmissible spongiform encephalopathy (TSE) pathogen is not inactivated under inactivation conditions of general infectious agents. The most effective inactivation method thereof is to heat the same in the presence of SDS at about 100° C. The conditions further enhance the protein solubilization in the above (2). It is presumed that the conformation of PrPres is disrupted under the conditions in the same manner as other proteins. However, other proteins remain soluble when a temperature is adjusted to be lower than room temperature, while PrPres regains the aggregation property. Due to this property, PrPres can be selectively precipitated.

As the conditions for achieving the above object, it is preferable that the SDS concentration should be 3% by weight, and heating should be performed at 100° C. for 10 minutes.

(3) Aggregation of PrPres

The proteins are made soluble by the above process. Infected animal-derived PrPres is aggregated and precipitated, and uninfected animal-derived PrPc and unrelated proteins remain soluble in a supernatant by cooling the processed product under a neutral condition. In order to achieve this object, it is preferable that cooling under a neutral condition should be performed by cooling to a temperature of −80° C. to 0° C. at a pH of 7.2 to 7.3.

(4) Separation of PrPres Aggregates

In order to separate precipitates of the PrPres aggregates which had been obtained under the neutral condition which were formed under an acidic condition, a centrifugal acceleration rate by high-speed centrifugation is sufficient, and a centrifugal acceleration rate by ultrahigh-speed centrifugation is not necessary. This point is remarkably different from a conventional presumption that PrPres is obtained only by ultrahigh-speed centrifugation. In addition, the specimen processing can be simplified because the PrPres aggregates can be obtained by high-speed centrifugation, not by ultrahigh-speed centrifugation. The acidic condition is preferably a pH of 4.5 to 4.6, and centrifugation step is preferably performed by high-speed centrifugation at a centrifugal acceleration rate of 10,000 to 20,000×g.

(5) Dissolution of Aggregates

It is necessary that the aggregates obtained in the above-described manner should be dissolved before detection or determination of PrPres. The aggregates are usually dissolved in a buffer used for the detection or determination. Examples of the buffer and dissolution conditions include a heating treatment of a suspension of the aggregates in the Laemli-SDS sample buffer at 100° C. for 10 minutes.

Detection or Determination

The present invention also relates to a method for detecting or determining abnormal prion protein (PrPres) associated with transmissible spongiform encephalopathy (TSE), wherein the abnormal prion protein (PrPres) in the processed specimen obtained by the above method is determined by immunoassay.

Three-fold serial dilution of rHaPrP (1 μg/ml) was performed. The detection limit of rHaPrP was determined by the ultrasensitive chemiluminescence method. It was confirmed that $4.4\times10^{-18}$ mole (presuming 23,000 g as the molecular weight of rHaPrP) or less was detectable.

Three-fold serial dilution of a uninfected hamster brain homogenate was performed. The detection limit of PrP in the brain homogenate was determined using an anti-PrP monoclonal antibody as a primary antibody, and an HRP-labeled anti-mouse IgG antibody as a secondary antibody. It was found that PrP molecules corresponding to those present in $10^{-9}$ g brain equivalent was detectable. It was indicated that after the infected and uninfected hamster brain homogenates had been subjected to the treatment with PK, both the brain homogenates were able to be clearly discriminated to each other, and it was confirmed that the molecules in the detected site were PrPres molecules.

After blood had been collected, plasma was separated, and the pretreatment with PK, and the step of heating with SDS were performed, whereby safety for operators and environment can be assured. At this stage, the plasma amount obtained from the collected blood was diluted by about five fold. 10 to 20 μL of the diluted plasma can be used as a generally used specimen. This corresponds to 2 to 4 μL of the initially collected blood.

The rate-limiting step in the specimen processing depends on the number of specimens to be processed at the same time. As a necessary amount of one specimen is extremely small in the method, a large number of specimens can be analyzed at the same time by processing the large number of specimen on a microplate at the same time.

After specimens had been fixed to the membrane by western blotting or dot blotting, the time required to complete the process using the primary antibody and secondary antibody, and the chemiluminescence process for analyzing luminescence intensity is one to two days. Compared with other proposed conventional methods, it is remarkably short. Therefore, the method is the most suitable for the blood test as routine testing.

The specimens which had been subjected to the treatment with PK and the acidic SDS precipitation method are fixed to the membrane by dot blotting or western blotting after electrophoresis, whereby the ELISPOT or western blotting analysis of the specimens becomes possible.

It becomes possible to quantify PrPres in the specimens by quantitative analysis of luminescence intensity of chemiluminescence in ELISPOT assay. Comparing with the conventional methods focusing on the presence of PrPres, the quantitative analysis of luminescence intensity is a significant advantage.

PrPres is highly likely to be formed into aggregates. It is presumed that the aggregates are formed by interaction of intramolecular sugar chains. There is a possibility that the aggregation occurs in the same molecule or occurs by interaction with other molecules. It is presumed that the aggregation is not observed after the intramolecular sugar chains were digested, and the ultrasensitive chemiluminescence method in the method of the present invention was used. However, subsequence study provided results by which it is suggested that free nucleic acid in blood may be significantly involved with this aggregation.

There are two significant points to detect abnormal prion protein (PrPres) in blood, i.e., (1) selective concentration or amplification of PrPres; and (2) use of a highly sensitive protein detection method. Therefore, it is preferable in the method of the present invention to use the acidic SDS precipitation method and the ultrasensitive chemiluminescence method. Normal proteins remain dissolved under the acidic SDS conditions, while as it is predicted that several molecules or some protein molecules of PrPres are aggregated, it is presumed that PrPres is precipitated under the conditions. Therefore, it is presumed that PrPres can be selectively precipitated.

It is extremely difficult to suppress the background luminescence in the ultrasensitive chemiluminescence method because the method is highly sensitive. However, as the background luminescence is produced by nonspecific attachment of the primary antibody and the secondary antibody to the membrane, if the background luminescence is sufficiently suppressed, the ultrasensitive chemiluminescence method is considered to be extremely effective. It is a significant point in the present invention that the background luminescence can be sufficiently suppressed.

Disclosure of a Specific Mode

An example of a specific mode of the method of the present invention is shown below.

(1) Selective Concentration Method of PrPres Acidic SDS Precipitation Method:

After a plasma specimen had been diluted in Tris buffer saline (containing 10 mM EDTA) by four fold so as to sufficiently decrease the protein concentration, the specimen is treated with proteinase K (PK) (2 mAnson unit/ml; 50 μg/ml) at 37° C. for 60 minutes to digest PK-sensitive proteins. 1/10 amount of 30% sodium lauryl sulfate (SDS) and 1/10 amount of 1 M dithiothreitol (DTT) are added, and the mixture is heated at 100° C. for 10 minutes to inactivate the infectivity of TSE.

After the specimen had been cooled, acidic saline (0.02 M acetic acid, 10 mM EDTA, and 0.15 M NaCl) in the equal amount to the amount of the specimen is added at 10° C., the mixture is mixed, and then is made stand still for five minutes. Next, after the specimen had been subjected to centrifugation at 15,000 rpm for 10 minutes, the precipitates are collected, and the supernatant is discarded. The precipitates are dissolved in Tris buffer saline (containing 5 mM EDTA, and 3% SDS). Acidic saline is added again, and precipitates are collected by the centrifugation operation. A large amount of SDS is removed from the collected precipitates by the methanol precipitation method, and then the precipitates are dissolved again in the Laemli-SDS sample buffer.

The important point in this process is to conduct a reaction of the plasma specimen dissolved in a buffer containing SDS with the acidic saline at 10° C. If the reaction time is 10 minutes or longer, SDS is crystallized, and the amount of adsorbed impurity proteins increases. Therefore, the reaction time at this step should be generally five minutes. EDTA (having a concentration of 5 mM) in the Tris buffer saline (containing 5 mM EDTA and 3% SDS) used for redissolving the specimen is an optional component, but it is effective to remove contaminant proteins.

(2) Highly-Sensitive Detection Method of PrPres (i)

The precipitates dissolved in the above (1) are subjected to western blotting using 15% gel electrophoresis and a PVDF membrane by a general technique. After the blotted membrane had been blocked by a blocking agent, it is reacted with a primary antibody (3F4 or other anti-PrP antibody), and a secondary antibody (HRP goat anti-mouse IgG) to make protein portions reacted with the antibodies luminescent using a highly-sensitive chemiluminescence reagent, and luminescence signals are detected and analyzed by an image analyzer.

(ii)

Dot blotting of the precipitates dissolved in the above (1) is prepared using PVDF or other blotting membrane.

The important point in this process is blocking to suppress the background luminescence such that the ultrasensitive chemiluminescence reagent can be used. The use of general BSA, casein or other blocking agent, produced by a manufacturer, alone is not sufficient in the blocking process, and thus a plurality of blocking agents are alternately used. Membrane portions which cannot be blocked by one blocking agent can be blocked in this operation. In addition, nonspecific attachment by each of the primary and secondary antibodies, due to the different properties thereof can be separately blocked. In the case of a water-soluble protein, a reagent which can detect $10^{-21}$ mole or less of the protein is used in highly-sensitive ultrasensitive chemiluminescence.

EXAMPLES

Next, the present invention will be further specifically explained with reference to examples.

Example 1

Detection Limit of rHaPrP by the Ultrasensitive Chemiluminescence Method

Three-fold serial dilution of rHaPrP, namely, a recombinant hamster prion protein (amino acids 23 to 231, manufactured by ALIKON Corp., Switzerland) using a buffer prepared by adding the equal amount of a superBlock blocking buffer (manufactured by PIERCE Corp.) to the Laemli-sample buffer was performed, while the diluent was heated. 10 μl of the diluent obtained at each dilution step was subjected to electrophoresis using an SDS-15% acrylamide gel, and western blotting on a polyvinylidene fluoride (PVDF) membrane, or 10 μl of the diluent obtained at each dilution step was subjected to dot blotting on the PVDF membrane. Anti-PrP monoclonal antibody 3F4 as the primary antibody and peroxidase-labeled goat anti-mouse IgG (HRPGAM) as the secondary antibody were used for the blotted PVDF membrane, and the detection limit of rHaPrP was determined by the ultrasensitive chemiluminescence system. The luminescence signals produced by chemiluminescence were detected by an image analyzer (LAS3000; manufactured by FUJIFILM Corporation). The detected luminescence signals were printed. The amount of the rHaPrP protein challenged to the electrophoresis gel or the amount of the dot-blotted protein is shown herein. The results thereof are shown in the upper portion of FIG. 1 and FIG. 6.

Three-fold serial dilution, electrophoresis, and western blotting using a 10% brain homogenate of a hamster infected with scrapie (strain sc237) by intracerebral inoculation were performed in the same manner as the above method. The same primary antibody and secondary antibody as those described above were used to determine the amount of the PrP protein in the brain homogenate by the chemiluminescence method. The results thereof are shown in the bottom portion of FIG. 1. "g Br.eq" represents the amount used for the electrophoresis analysis of the sample at each dilution step in terms of the brain equivalent.

It is presumed that the PrP protein in the brain homogenate was detected (lanes 1 to 4, around 19 to 35 kDa) as a plurality of protein bands (mainly three bands of a disaccharide chain, a monosaccharide chain, and a non-saccharide chain), based on the presence of sugar chains. However, aggregates with proteins other than PrP, depending on the presence of sugar chains (lanes 1 to 3, around 37 kDa or higher), and molecules that had a relatively reduced molecular weight (lanes 1 and 2, around 16 kDa) because they had been partially cut were detected at the same time.

Example 2

Figure 2:
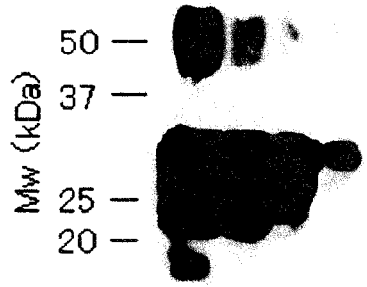
Figure 2:
Figure 2:
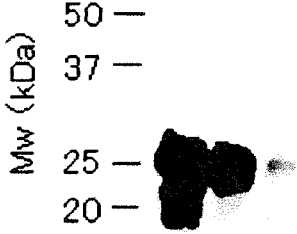

Discrimination of Infection from Uninfection by the Pretreatment with Proteinase K in Hamster Brain Homogenates 10% brain homogenate of infected or uninfected hamster was subjected to low-speed centrifugation. Three-fold serial dilution of a sample that had been subjected to the pretreatment with proteinase K (PK) (the bottom portion) (2 units, 37° C., 60 minutes) or a sample that had not been subjected to the pretreatment (the upper portion) was performed. PrP in samples was detected by electrophoresis, western blotting, and the chemiluminescence method using 3F4-HRPGAM. FIG. 2 shows the results thereof. Regarding the samples that had not been subjected to the treatment with PK, there was a difference in the amount of proteins between infected and uninfected hamster samples, but there were bands detected in both the samples, and thus the difference cannot be said to be an absolute difference (the upper portion).

However, regarding the samples that had been subjected to the treatment with PK, infected hamsters can be clearly discriminated from uninfected hamsters, based on the presence or absence of PrP (the bottom portion). This is the difference between infection and uninfection using the brain homogenate as conventionally proposed, but it clearly showed that they were able to be discriminated by the ultrasensitive chemiluminescence method (PrP detected after the PK treatment is represented by PrPres which means PK-resistant PrP).

Example 3

Figure 3:
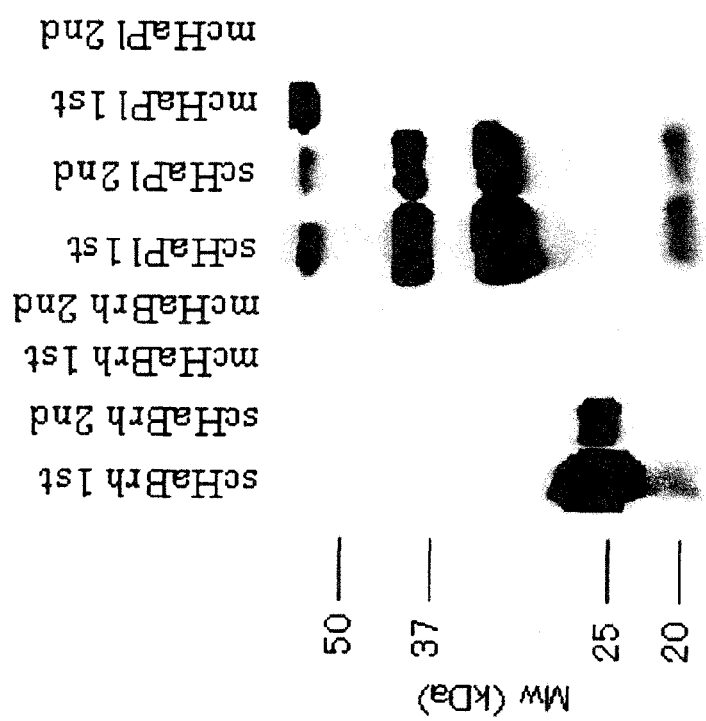
Figure 3:
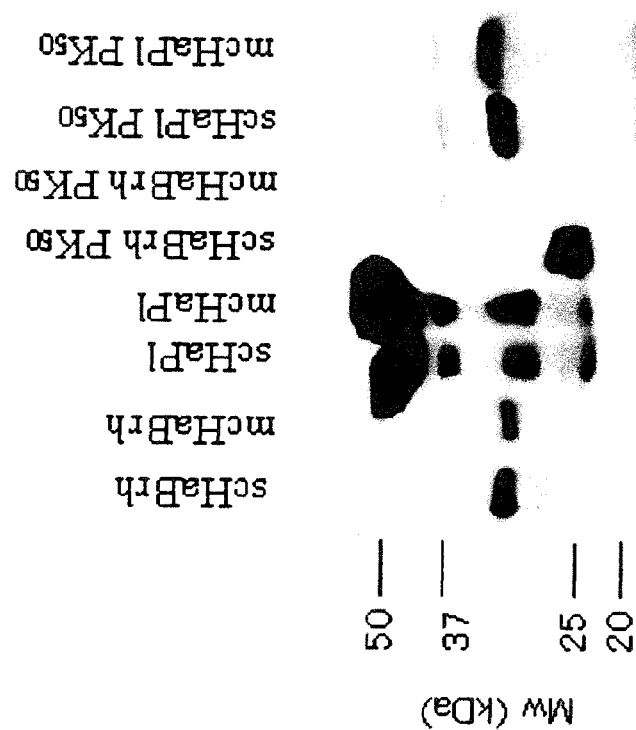

Discrimination of Scrapie Infection from Uninfection by the Acidic SDS Precipitation Method in Hamster Plasma Specimens 10% brain homogenate of an infected or uninfected hamster (scHaBrh or mcHaBrh), or infected or uninfected hamster plasma (scHaPl or cHaPl) was subjected only to the PK treatment (2 units, 37° C., 60 minutes) (Panel A) or the PK treatment and the acidic SDS precipitation method (SDS concentration of 3%, 10° C., three minutes) (Panel B), and then SDS electrophoresis-western blotting was performed to detect protein bands by the ultrasensitive chemiluminescence method. The results thereof are shown in FIG. 3.

Panel A

The electrophoresis pattern of each specimen that had been subjected only to the PK treatment (each sample represented by PK50) was compared by the ultrasensitive chemiluminescence method. Discrimination of infection from uninfection in the samples that had not been subjected to the PK treatment was not possible (lanes 1 to 4). Discrimination of infection from uninfection in the 10% brain homogenate samples by the PK treatment was possible (lanes 5 and 6), but the discrimination in plasma was not possible (lanes 7 and 8).

Panel B

After each of all the above samples had been subjected to the PK treatment (2 units, 37° C., 60 minutes), the samples were processed by the acidic SDS precipitation method (SDS 3%, 10° C., three minutes) (once or twice; represented by $1^{st}$ or $2^{nd}$), and the SDS electrophoresis patters thereof were compared. Discrimination of infection from uninfection in the 10% brain homogenates was possible by the acidic SDS precipitation method (lanes 1 to 4). Discrimination of infection from uninfection in plasma was possible by adding the acidic SDS precipitation method, but in the $1^{st}$ process, a band of mcHaPl in the region higher than 50 KDa was confirmed. The band disappeared after the acidic SDS precipitation method was performed twice. Therefore, it was possible to discriminate infection from uninfection in a case using plasma samples by combining the PK treatment with the acidic SDS precipitation method (lanes 5 to 8).

The above results indicate that when the brain homogenate was used as a specimen, it was possible to discriminate infection from uninfection in the specimen only by the PK treatment, while when plasma was used as a specimen, it was possible to discriminate infection from uninfection by the acidic SDS precipitation method in addition to the PK treatment.

Example 4

Figure 4:
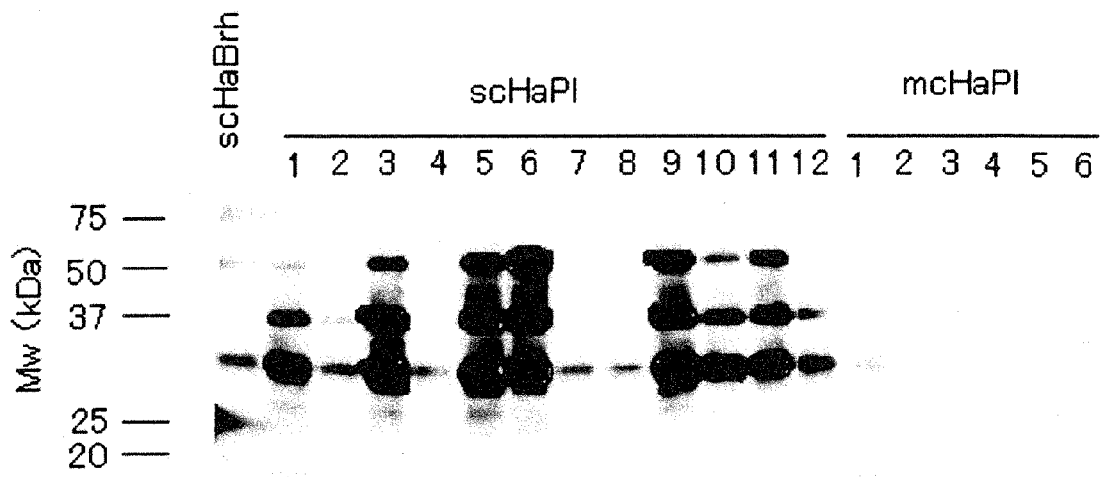

Discrimination of Scrapie Infection from Uninfection by the Acidic SDS Precipitation Method in a Plurality of Hamster Plasma Specimens After plasma of scrapie infected hamsters (12 hamsters) and uninfected hamsters (6 hamsters) had been subjected to the PK treatment (2 units, 37° C., 60 minutes) and the acidic SDS precipitation method (SDS concentration of 3%, 10° C., three minutes), the electrophoresis pattern of each sample was compared by the ultrasensitive chemiluminescence method applied to the western blotted membrane prepared using the primary antibody 3F4 and the secondary antibody HRPGAM. As a control, 10% brain homogenate of the infected hamster was subjected to the same processing, and the pattern thereof was represented in a comparative lane (lane 1). The results thereof are shown in FIG. 4.

Regarding infected hamster plasma, bands were observed in all the plasma samples, while regarding uninfected hamster plasma, only a dilute band was observed in plasma samples No. 1 and No. 6. The acidic SDS precipitation method was performed only once for the samples herein, and thus it is expected that the dilute band observed in uninfected hamster plasma No. 1 and No. 6 may disappear by performing the acidic precipitation methods twice, in the same manner as shown in Panel B of Example. Accordingly, it is possible to discriminate an infected hamster from a uninfected hamster using plasma samples thereof by the combination of the PK treatment with the acidic SDS precipitation method.

The electrophoresis patters of the infected hamster brain samples and plasma samples were slightly different. Therefore, it was a little concerned that the protein observed in plasma may be different from that in the brain (consequently, the protein may not be PrPres). In addition, it was a little concerned whether discrimination of infection from uninfection was appropriate.

Example 5

Appearance of the Similar Pattern of Infected Hamster Plasma by Mixing Infected Hamster Brain Homogenate with Uninfected Hamster Plasma The above concerns were able to be dispelled by the data of Example 5.

Figure 5:
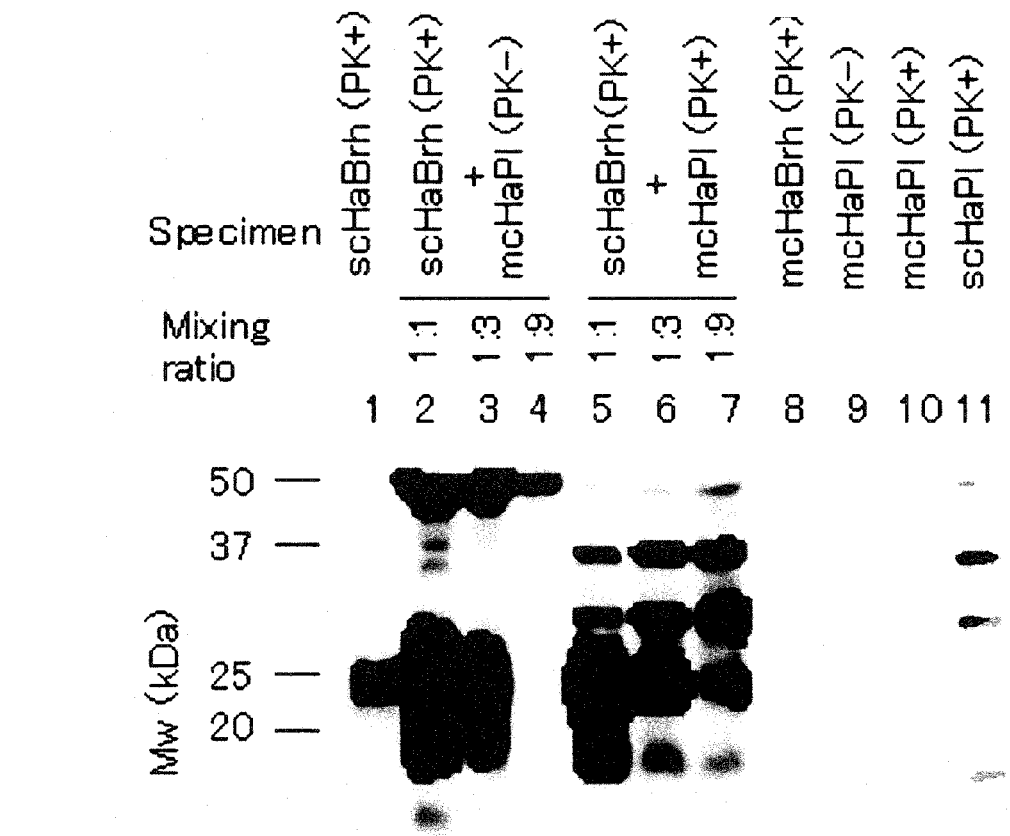

After the infected hamster brain homogenate was mixed with the uninfected hamster plasma samples, and the mixtures were subjected to the acidic SDS precipitation method, the electrophoresis patterns thereof were compared by the same detection method. The results thereof are shown in FIG. 5. It was found that the electrophoresis pattern (lane 1) of the infected brain homogenate and the electrophoresis pattern of the infected hamster plasma (lane 11) were completely different. No protein band was observed both in the brain homogenate and plasma of the uninfected hamster (lanes 8 to 10).

However, extremely similar patterns (lanes 5 to 7) to the electrophoresis pattern of the infected hamster plasma were obtained by mixing the infected hamster brain homogenate with the uninfected hamster plasma. Therefore, it is presumed that the pattern (lane 11) was observed in the infected hamster plasma because aggregates of PrPres with some kind of plasma proteins had been formed. It was shown that the obtained electrophoresis patterns of the samples were different, depending on the mixture ratio of the plasma protein to PrPres in the brain. It can be presumed that the difference in electrophoresis pattern of the infected hamster individual was resulted from the difference in the amount ratio of the plasma protein formed into aggregates to Prepres in blood.

Example 6

Figure 6:
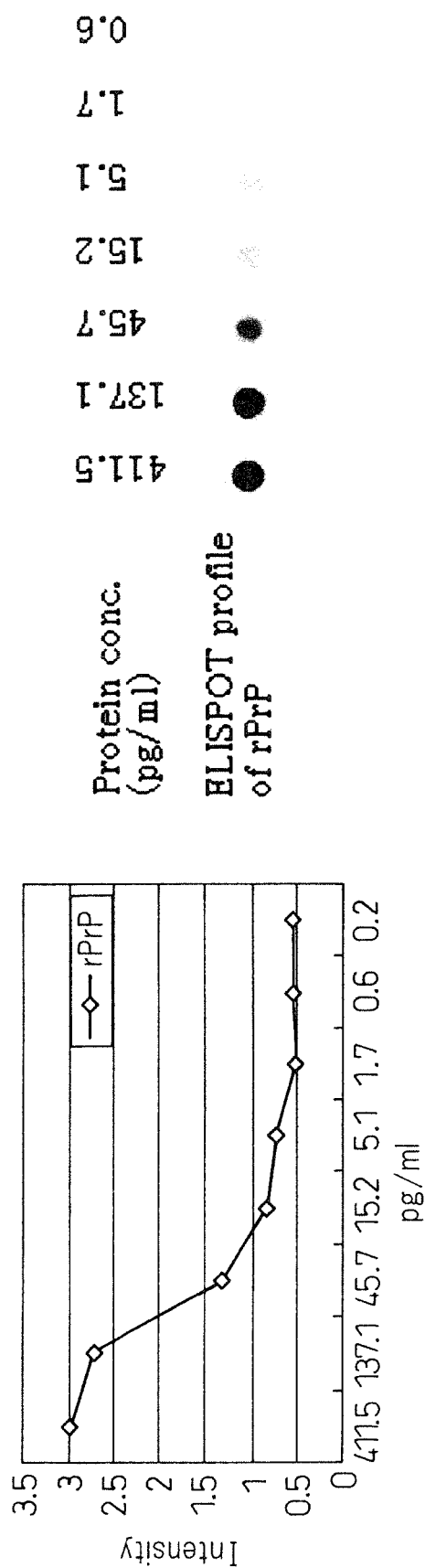

Detection Limit of PrP by the Ultrasensitive Chemiluminescence Method (1) rHaPrP was subjected to three-fold serial dilution, and dot blotting. The luminescence intensity of each of the obtained spots was detected using the chemiluminescence method by ELISPOT with the primary antibody 3F4 and the secondary antibody HRPGAM. The results thereof are shown in the right portion of FIG. 6. The chemiluminescence intensity of each spot was determined to prepare a two-dimensional graph showing the chemiluminescence intensity and the protein concentration. The results thereof are shown in the left portion of FIG. 6. This graph indicates that at least 5 pg/ml PrP or an absolute amount of 0.1 pg or less of PrP was able to be detected.

Figure 7:
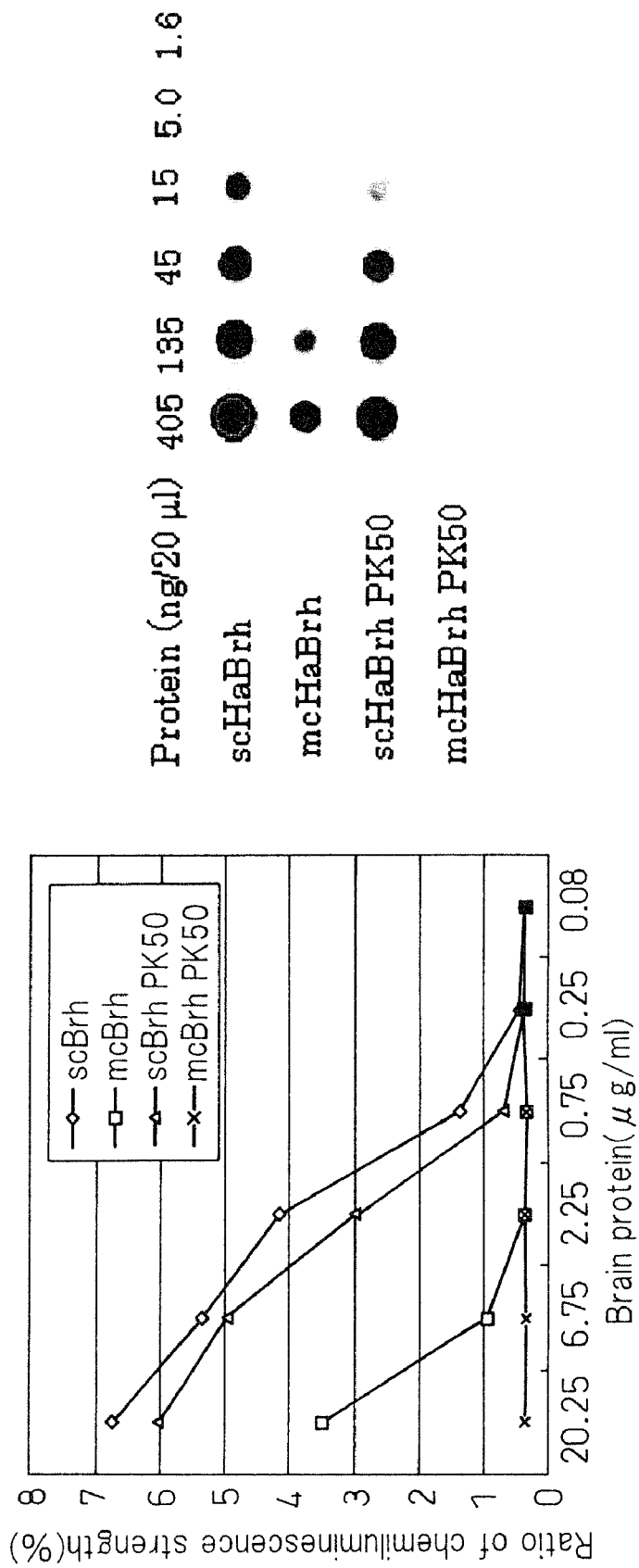

(2) The infected or uninfected hamster brain homogenate (scHaBrh or mcHaBrh) and each homogenate which had been subjected to the PK treatment (two units, 37° C., 60 minutes) (PK50) were subjected to three-fold serial dilution and chemiluminescence detection by ELISPOT. The PrP amount in each brain homogenate was able to be quantified by the above procedures. The results thereof are shown in FIG. 7. It is predicted that the PrP protein amount in the brain of scHaBrh would be about 1 mg/g Brh, referring to the curve in FIG. 6 as a standard curve. It is presumed that PK resistant PrP (PrPres) would account for most of the amount thereof. On the other hand, the PrP amount in the uninfected hamster brain homogenate was about $\frac{1}{10}$ with respect to the PrP amount in the brain of the infected hamster. It is presumed that the PK-sensitive molecule ($PrP^c$) would account for most of the entire amount thereof.

The invention claimed is:

1. A method of pretreating a specimen that will be tested to determine or detect the presence of abnormal prion protein (PrPres) associated with transmissible spongiform encephalopathy (TSE), comprising the steps of:
    (1) adding sodium dodecyl sulfate (SDS) to the specimen, wherein the pH of the specimen is neutral, and heating the specimen comprising the SDS to dissolve proteins in the specimen;
    (2) cooling the specimen treated in step (1) to aggregate the PrPres; and
    (3) adding an acidic solution to the specimen made in step (2) and mixing the specimen to acidify the specimen.

2. The method according to claim 1, wherein the specimen is treated with a protease before the step (1).

3. The method according to claim 1, wherein the sodium dodecyl sulfate concentration at the above step (1) is 3% by weight.

4. The method according to claim 1, wherein heating at the above step (1) is performed at 100° C. for 10 minutes.

5. The method according to claim 1, wherein the cooling in step (2) is performed by cooling to a temperature of 0° C. to −80° C. at a pH of 7.2 to 7.3.

6. The method according to claim 1, wherein separation of the acidified aggregate PrPres is performed by centrifugation following the above step (3).

7. The method according to claim 1, wherein the pH of the acidified specimen is 4.5 to 4.6.

8. The method according to claim 6, wherein the centrifugation is performed by high-speed centrifugation at a centrifugal acceleration rate of 10,000 to 20,000×g.

9. The method according to claim 1, wherein the aggregate obtained at the above step (3) is dissolved in a buffer.

* * * * *